United States Patent
Bratincsak

(10) Patent No.: US 12,257,059 B2
(45) Date of Patent: Mar. 25, 2025

(54) ELECTROCARDIOGRAM EVALUATION USING Z-SCORE BASED STANDARDS

(71) Applicant: Andras Bratincsak, Honolulu, HI (US)

(72) Inventor: Andras Bratincsak, Honolulu, HI (US)

(73) Assignee: Andras Bratincsak, Honolulu, HI (US)

( * ) Notice: Subject to any disclaimer, the term of this patent is extended or adjusted under 35 U.S.C. 154(b) by 796 days.

(21) Appl. No.: 16/849,994

(22) Filed: Apr. 16, 2020

(65) Prior Publication Data

US 2021/0321896 A1  Oct. 21, 2021

(51) Int. Cl.
*A61B 5/349* (2021.01)
*A61B 5/00* (2006.01)
(Continued)

(52) U.S. Cl.
CPC .............. *A61B 5/349* (2021.01); *A61B 5/352* (2021.01); *A61B 5/364* (2021.01); *A61B 5/366* (2021.01);
(Continued)

(58) Field of Classification Search
CPC ......... A61B 5/316; A61B 5/364; A61B 5/352; A61B 5/366; A61B 5/743; G16H 50/30; G16H 50/70; G16H 50/20
See application file for complete search history.

(56) References Cited

U.S. PATENT DOCUMENTS

| | | | |
|---|---|---|---|
| 5,092,341 A | 3/1992 | Kelen | |
| 6,223,073 B1 | 4/2001 | Seegobin | |

(Continued)

FOREIGN PATENT DOCUMENTS

| | | |
|---|---|---|
| CN | 107811626 A | 3/2018 |
| CN | 109907733 A | 6/2019 |

(Continued)

OTHER PUBLICATIONS

Chubb Henry et al: "A proposed method for the calculation of age-dependent QRS duration z-scores", Journal of Electrocardiology., vol. 58, Jan. 1, 2020 (Jan. 1, 2020), pp. 132-134, XP055820353 (Year: 2020).*

(Continued)

*Primary Examiner* — James M Kish
*Assistant Examiner* — Laura Hodge
(74) *Attorney, Agent, or Firm* — Rupam Bhar; Calderon Safran Wright PC

(57) ABSTRACT

A system and methods for the assessment of cardiac status of a subject are provided. In embodiments, a method includes an electrocardiogram (ECG) machine recording electrical ECG information for a plurality of ECG variables from an examined subject; digitally transforming the electrical ECG information to digital values of the ECG variables; comparing the digital values of the ECG variables from the examined subject with normative data stored in a database, wherein the normative data is based on healthy individuals; assigning predictive Z-scores to the digital values of the ECG variables based on the normative data; establishing a diagnosis of the examined subject based on a determination that the predictive Z-scores are within normal limits or are outside normal limits of the normative data; and generating a report including the diagnosis of the examined subject.

18 Claims, 13 Drawing Sheets

(51) Int. Cl.
  *A61B 5/352*   (2021.01)
  *A61B 5/364*   (2021.01)
  *A61B 5/366*   (2021.01)
  *G16H 10/60*   (2018.01)
  *G16H 20/10*   (2018.01)
  *G16H 50/20*   (2018.01)
  *G16H 50/30*   (2018.01)
  *G16H 50/70*   (2018.01)

(52) U.S. Cl.
  CPC ............ *A61B 5/743* (2013.01); *G16H 10/60* (2018.01); *G16H 20/10* (2018.01); *G16H 50/20* (2018.01); *G16H 50/30* (2018.01); *G16H 50/70* (2018.01)

(56) References Cited

U.S. PATENT DOCUMENTS

| | | | |
|---|---|---|---|
| 9,801,562 B1 | 10/2017 | Host-Madsen | |
| 2003/0176802 A1* | 9/2003 | Galen | A61B 5/339 600/523 |
| 2009/0043218 A1 | 2/2009 | Warner et al. | |
| 2010/0217144 A1* | 8/2010 | Brian | G16H 50/30 600/523 |
| 2016/0256064 A1 | 9/2016 | Esters, Jr. | |
| 2017/0188932 A1 | 7/2017 | Singer et al. | |
| 2019/0167143 A1* | 6/2019 | Li | A61B 5/361 |
| 2020/0260980 A1* | 8/2020 | Liu | A61B 5/352 |

FOREIGN PATENT DOCUMENTS

| | | | |
|---|---|---|---|
| CN | 110688942 A | | 1/2020 |
| CN | 111743531 A | | 10/2020 |
| KR | 102216047 B1 | | 2/2021 |
| WO | 2013123549 A1 | | 8/2013 |
| WO | 2015187401 A1 | | 12/2015 |
| WO | 2020049571 A1 | | 3/2020 |

OTHER PUBLICATIONS

Davignon et al.—ECG Standards for Children; Ped Cardiol 1: pp. 133-152 (1979/1980).

Macfarlane et al.—Paediatric Normal Limits; Comprehensive Electrocardiology, DOI 10.1007/978-1-84882-046-3_A2 © Springer-Verlag London Limited 2011; pp. 2128-2195.

Rijnbeek et al.—New normal limits for the paediatric electrocardiogram; European Heart Journal (2001) 22, pp. 702-711.

Saarel et al.—Electrocardiograms in Healthy North American Children in the Digital Age; Circ Arrhythm Electrophysiol. 2018; 11:e005808. DOI: 10.1161/CIRCEP.117.005808; pp. 1-8.

International Search Report and Written Opinion issued in the corresponding Application No. PCT/US2021/027057 on Jul. 22, 2021.

Chubb Henry et al: "A proposed method for the calculation of age-dependent QRS duration z-scores", Journal of Electrocardiology., vol. 58, Jan. 1, 2020 (Jan. 1, 2020), pp. 132-134, XP055820353.

* cited by examiner

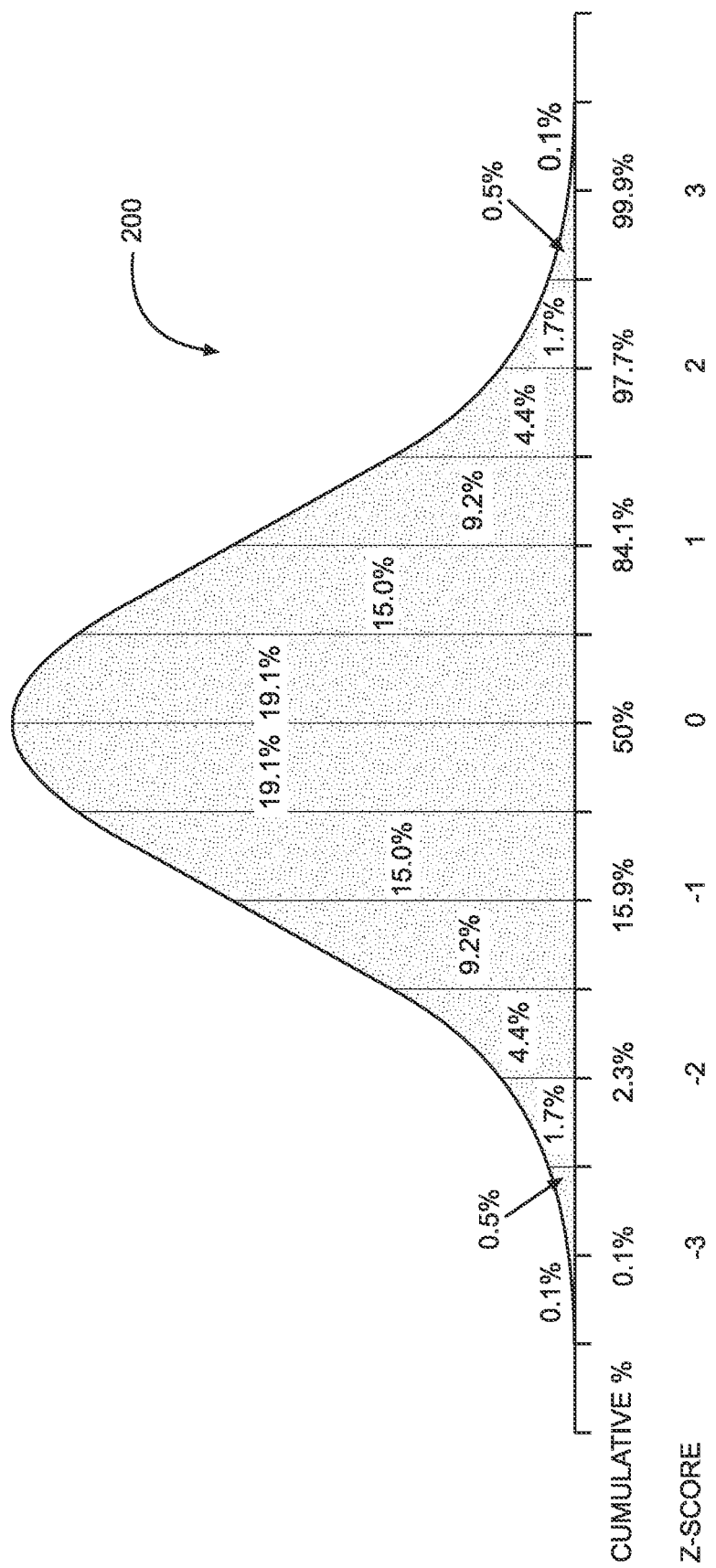

Page 2: values of ECG variables with corresponding z-scores

Abnormal variables: SV1: 2.3 MV (z 3.11), RV5: 3.2 MV (Z 2.85) RV6: 2.7 MV (z 2.02)

Demographics: female, 11 y/o, Wt: 97.4 Kg, Ht: 170.5 cm, BSA: 2.15 m2

Normal variables:
HR: 84 bpm (Z - 0.30);
P axis: -1 degrees (Z -1.98); QRS axis: 13 degrees (Z -1.89);
T axis: 18 degrees (Z -1.21); R-T axis deviation: 5 degrees (Z -1.60);
PR interval: 140 msec (z 0.19); QRS duration: 98 msec (Z 1.34);
QTc (Bazett): 451 msec (Z 0.87);

Amplitudes (mV):
Lead I P 0.1 Q 0.2 R 1.8 S nT 0.3
Lead II P 0.0 Q n R 0.5 S 0.3 T 0.2
Lead III P -0.1 Q n R 0.5 S 1.3 T  -0.1
Lead aVR p -0.1 Q 1.8 R n S N T -0.2
Lead aVL p 0.1 Q 0.2 R 1.4 S N T 0.2
Lead aVF p 0.0 Q n R 1.2 S 0.8 T 0.1

Lead v1 p 0.0 Q n r 0.4 S 2.3 T 0.1
Lead v2 P 0.1 Q n R 0.6 S 2.6 T 0.6
Lead v3 P 0.0 Q n R 1.0 S 1.1 T 0.2
Lead v4 P 0.0 Q n R 2.6 S 0.8 T -0.0
Lead v5 P 0.0 Q n R 3.2 S 0.6 T 0.0
Lead v6 P 0.0 Q n R 2.7 S 0.4 T 0.1

Diagnosis and predictive scores

Based on the abnormal variables with Z-scores outside -2 To 2 range: SV1, RV5 and RV6, the following diagnoses are suggested

1. Left ventricular hypertrophy
Predictive value of suggested diagnoses:
1. SV1 Z-score above 2 for LVH has a 70% specificity and 65% sensitivity based on Bratincsak et al. PMID 25600360

FIG. 6B

ELECTROCARDIOGRAM EVALUATION USING Z-SCORE BASED STANDARDS

BACKGROUND

The electrocardiogram (ECG) is used to detect the electrical properties of the heart. The ECG is obtained by connecting electrical wires to 12-15 specific locations on the chest and extremities. The ECG machine detects the electrical forces generated by the heart. Every heart beat creates an identifiable and quantifiable sequence of electrical signals. These electrical signals are recorded and labeled as P, Q, R, S, T and U waves, corresponding to specific sequences of the heart cycle. See, for example, the electrical signals depicted in the ECG of FIG. 1. Each wave has values of amplitude, duration and characteristic shape and there are intervals between the waves, as depicted in the example of FIG. 1.

The assessment of an ECG is based on the complex evaluation of the multiple parameters derived from the qualitative and quantitative values of each wave (PQRSTU) and the intervals (RR, PR, QRS, ST, QT) between the waves measured over each of the 12 leads. Depending on the parameters derived from the measured values, clinicians can develop an ECG diagnosis.

In order to evaluate the ECG and present a diagnosis, medical professionals need to know the normal values of all waves and intervals. Normative ECG values were first established in 1954 for adults and in 1978 for children. Unfortunately, these normative standards even today are based on very few subjects, sometimes as few as 80 persons in an age group. Despite recent advantages of computer technology, clinicians have to still use the same almost 40-year-old standards for the assessment of ECG.

The many waves and intervals multiplied by the different leads generate more than one hundred ECG variables. Health care professionals have to decide whether an ECG value falls within or outside the normal limits based on their knowledge of different historical datasets and their respective ranges of normal values based on very few normal individuals. The current ECG machine is not able to produce an absolute determination of normalcy and abnormality of the many ECG variables, and therefore there is a significant difference and interpersonal variation in the subjective interpretation of ECGs.

Most importantly, so far, there is no development or utilization of any so called Z-scores for the expression of standard normal ECG values differentiating normalcy from abnormal values. The lack of availability of Z-scores for ECG does not allow the current ECG machines to make a diagnosis by the assessment of normal vs abnormal values of ECG variables, and therefore the accuracy and assessment of ECGs are completely based on the knowledge and accuracy of the medical professionals. Unfortunately there are very few highly trained medical professionals, so called electrophysiologists (specialized cardiologists) in the United States and the world, who can provide accurate ECG readings. The lack of a machine-based, automated and reproducible ECG interpretation results in the significant individual differences in the evaluation of ECGs by the wide array of medical professionals involved in the evaluation of ECGs. This suboptimal situation cannot be solved without the invention and development of a reliable automated system. The current inconsistent evaluation of ECGs in the young may result in misdiagnosis of life threatening heart conditions, and prevents the development of large-scale screening programs utilizing ECGs and undermine universal ECG screening.

SUMMARY

The present invention entails the application of innovative ECG evaluation for the diagnosis of cardiac problems and the prevention of adverse cardiac events, such as sudden cardiac death. The innovative ECG evaluation is based on novel normative ECG standards for 102 ECG variables from the largest historical cohort of 27085 healthy subjects. The upper and lower limits of ECG variables are correlated to Z-scores to provide an objective determination of normalcy and abnormality. The novel normative ECG standards from the largest historical cohort and the expression of cut-off values as Z-scores lend standardized and reproducible limits of ECG variables, and create the foundation of accurate ECG readings based on novel nomograms. A new ECG machine is designed to house the database with these new normal values and nomograms. The database on the ECG machine is interfaced to a computer algorithm using adaptive confirmatory enhancement (ACE) module. The computer system compares the data of an examined subject to the nomograms of the database in order to discern normal and pathologic values of 102 ECG variables, and to suggest an objective, reliable and reproducible ECG diagnosis for the evaluating medical team. This new ECG machine is then able to provide a Novel Extended ECG Report (NEER) including an additional page containing all 102 ECG variables with attributed Z-scores and suggested diagnosis. This NEER, based on the largest cohort ever compiled, provides the first detailed, truly quantitative assessment of ECG variables in the young. The expression of ECG variables in Z-scores now lends an objective and reproducible evaluation with simplified determination of normalcy and abnormality, and will lead to improved automated ECG readings in high volume cardiac screening efforts once correlated with confirmed diagnoses. The accurate detection of cardiac pathology through large scale screening efforts allows the development of stratified personalized medical management with recommendations for exercise allowance and medications for the prevention of sudden cardiac events.

BRIEF DESCRIPTION OF THE DRAWINGS

FIG. 2 depicts an exemplary distribution of percentages and cumulative percentages with corresponding Z-scores in a standard bell curve, according to aspects of the invention.

FIGS. 6A and 6B illustrate exemplary pages and content of a Novel Extended ECG Report (NEER), in accordance with embodiments of the invention.

DETAILED DESCRIPTION OF THE INVENTION

The detailed description of the invention comprises of the following parts: 1) an ECG database and nomograms; 2)

innovative Z-scores corresponding to ECG values; 3) predictive models with Z-scores for all 102 ECG variables; 4) a novel ECG machine; 5) a computer interface with adaptive confirmatory enhancement (ACE) module for ECG analysis; 6) a Novel Extended ECG Report (NEER); 7) utilization of the novel ECG system for diagnosis and screening; 8) innovation of the invention; 9) significance of the invention; and 10) potential industrial application and change in practice.

ECG Database and Nomograms

The innovative ECG evaluation with Z-scores according to embodiments of the invention is based on the largest historical cohort of healthy individuals ever compiled. The digital database contains data from 27085 subjects, none of which had a known heart condition or diagnosis of a cardiac disorder. Therefore, the entire cohort provides a reliable standard for normal values. The database of normative data is derived from 27085 subjects between the ages of 0 days and 40 years, a total of 23064 children and 4021 adults, 49% of which are female and 51% of which are male, from a wide range of ethnicities.

In order to adjust for the changes occurring throughout the development of ages of children and young adults, ECG variables are separated in 16 age groups as follows: 0-7 days, 1-4 weeks, 5-12 weeks, 3-5 months, 6-11 months, 12-23 months, 2-3 years, 4-5 years, 6-7 years, 8-9 years, 10-11 years, 12-13 years, 14-15 years, 16-18 years, 18-21 years, and adults 21-39 years of age. The database contains standard demographic variables from every subject including age, gender, weight, height, body surface area (BSA) and ethnicity.

The database contains digital data on 102 ECG variables of all 27085 subjects. The data reflects the standard 12-lead ECG protocol (leads I, II, III, aVR, aVL, aVF, V1, V2, V3, V4, V5, V6). The database stores digitally transformed data of the electronically obtained ECG information, unfiltered, at 500 Hz frequency. The 102 ECG variables include, but are not limited to the following: heart rate, RR interval, P wave axis, R wave axis, T wave axis, R-T wave axis deviation, PR interval, QRS interval/duration, QT interval, QTc interval calculated using automated Bazett, Framingham, and Friderica formulas, P and T wave amplitudes (in leads I, II, III, aVF, V1 and V6), Q, R, and S wave amplitudes in all 12 leads (leads I, II, III, aVR, aVL, aVF, V1, V2, V3, V4, V5, V6), Q, R and S wave areas, QRS integral and T wave integral (in leads I, II, III, aVF, V1 and V6).

Figure 1:
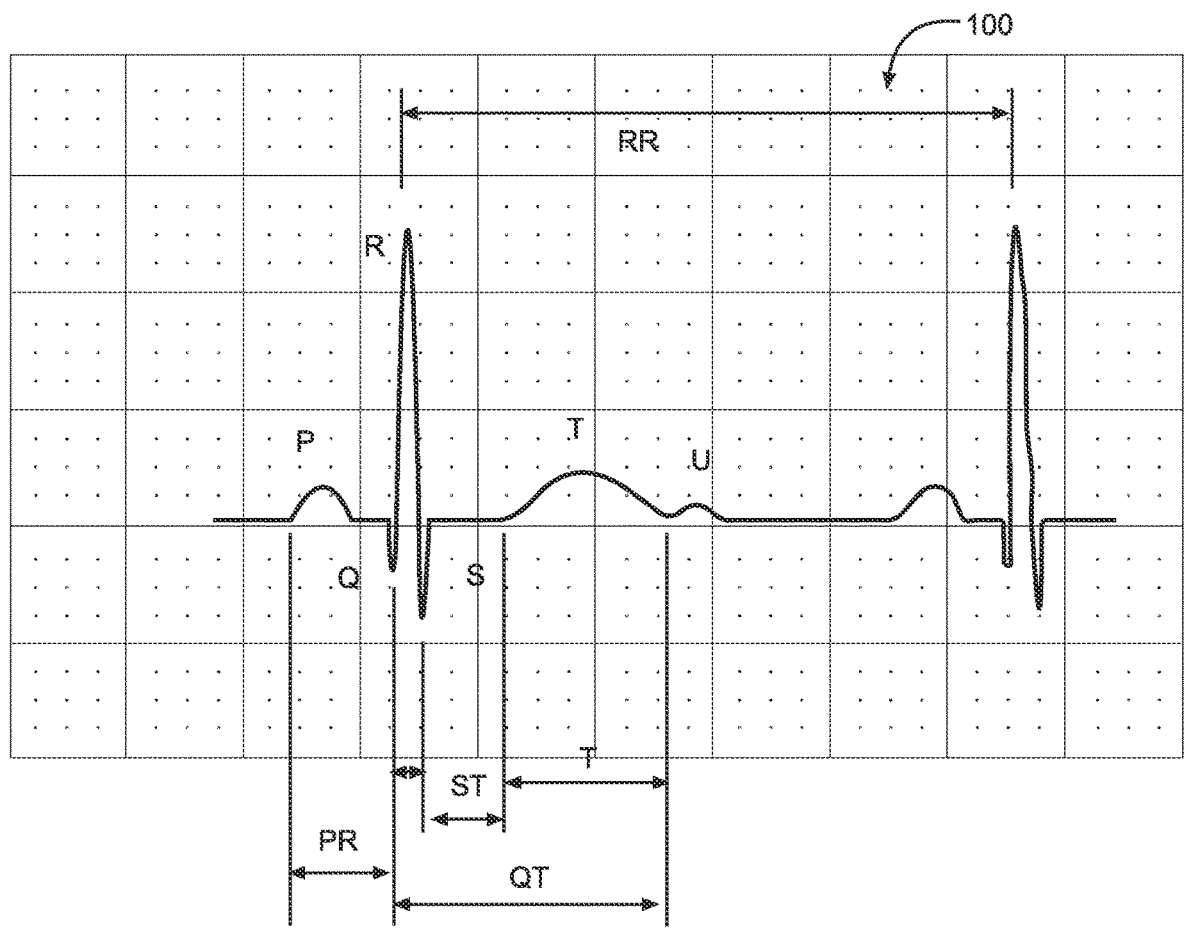
FIG. 1 is an exemplary graphical representation of ECG waves and intervals.

FIG. 1 depicts an exemplary graphical representation of ECG waves and intervals. The ECG captures the heart electrical activity. The electrical waves are denominated as P, Q, R, S, T and U waves. The P wave represents atrial depolarization, QRS waves represent ventricular depolarization, and T and U waves represent ventricular repolarization. The intervals between waves (represented at 100, for example) are important markers of the heart's activity and are measured as RR interval, PR interval, QRS duration, ST segment and QT interval.

The digital database is built by storing the data of 102 ECG variables in 27085 subjects resulting in a total of 2,762,670 digital data points. The data is then congregated into 16 age groups and 2 genders to create a graphical display of normal values, called nomograms. The digital database contains 3264 nomograms, 1 for each of the 102 ECG variables for each of the 16 age groups and for each gender. Every such nomogram contains data from 600-3000 individuals and serves as a normal standard for that age group and gender.

Innovative Z-Scores Corresponding to ECG Values

Developing Z-scores corresponding to ECG variables immediately presents an easy-to-interpret cut-off value to health care professionals separating normal and abnormal values.

Mean, standard deviation from the mean, and distribution are calculated from the 2,762,670 data points for each of the 102 ECG variables in each of the 16 age groups and for each gender. Since the database contains data from a normal cohort and the data is normally distributed, values ranging from 2 standard deviations below the mean and 2 standard deviations above the mean contain 95.4% of all values, and values ranging from 2.5 standard deviations below the mean and 2.5 standard deviations above the mean contain 98.8% of all values. Distinction of normalcy from abnormal values is accepted at 2 standard deviations from the mean in both negative and positive directions, therefore the cut-off for normal values corresponds to a Z-score of −2 or a Z-score 2 (See FIG. 2, for example). Normal values for the ECG variables then correspond to a range within the Z-score of −2 and 2. The values of normative ECG standards are then expressed as Z-scores: −2.5, −2, −1, 0, 1, 2, and 2.5 corresponding to $0.6^{th}$, $2.3^{rd}$, $15.9^{th}$, $50^{th}$, $84.1^{st}$, $97.7^{th}$ and $99.4^{th}$ percentiles for all ECG variables.

Expression of all 102 ECG variables for each of the 16 age groups in each gender can now be simply converted to Z-scores. The automated generation of Z-score for every ECG variable can immediately show whether the value is within or outside of the normal range, since a Z-score less than −2 or a Z-score more than 2 is considered abnormal. The innovative use of Z-scores for ECG values for the first time in history creates a reliable and consistent determination of normalcy within our database.

FIG. 2 depicts an exemplary distribution of percentages and cumulative percentages with corresponding Z-scores in a standard bell curve 200. Many data derived from populations or health assessments can be depicted as a normally distributed dataset. The mean represents the $50^{th}$ percentile of the group. Standard deviations from the mean are represented in both negative and positive directions corresponding to Z-scores of −3, −2, −1, 1, 2 and 3. The percentage of the population and the cumulative percentage can be followed at the points of standard deviation and Z-scores.

Predictive Models with Z-Scores for all 102 ECG Variables

Figure 3A:
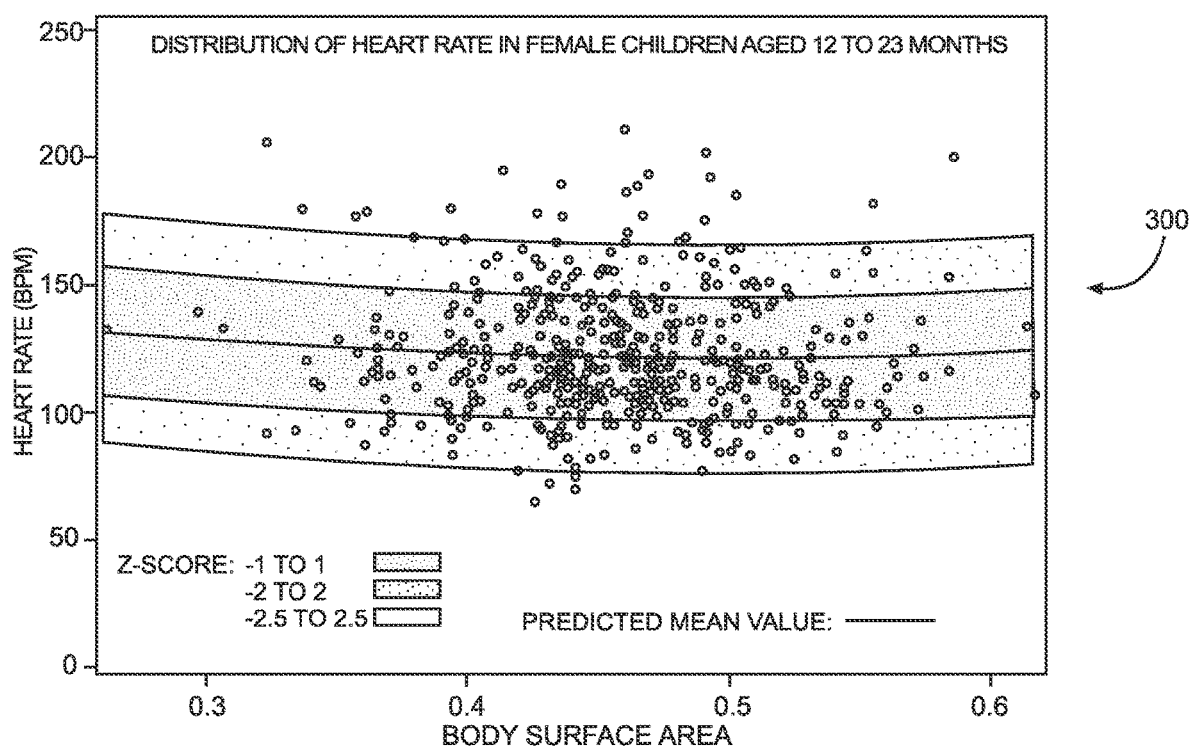
FIG. 3A is an exemplary graphical representation of a distribution pattern of heart rate in female children aged 12 to 23 months, according to aspects of the invention.
Figure 3B:
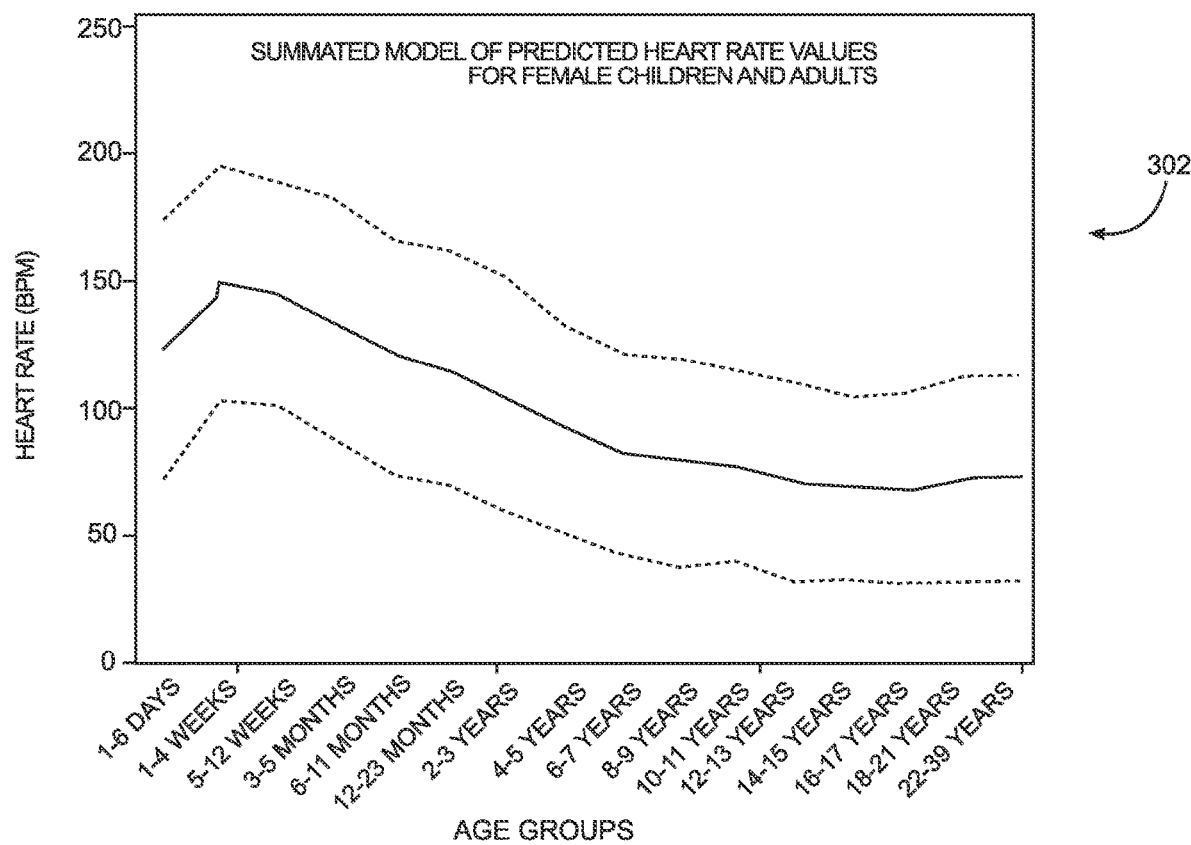
FIG. 3B depicts an exemplary summated model of predicted heart rate values for female children and adults, according to aspects of the invention.

Every single measured ECG variable (in relationship to BSA) is depicted as a graph creating a nomogram. An example of a single nomogram 300 for heart rate measurement along the ages of development can be seen in FIG. 3A, and an example of a continuous graph 302 of normal data along the ages of development can be seen in FIG. 3B. In the example of FIG. 3A, the distribution of heart rate in a single age group (12-23 months old females, n=491) based on BSA was used to develop the predicted value curve and Z-score brackets (−1 to 1, −2 to 2, and −2.5 to 2.5). In the example of FIG. 3B, the summated model of predicted values from the 16 age groups demonstrates the change in average heart rate along 0-39 years.

Analysis is performed and the results are expressed with genders separated, because of significant gender-specific differences in numerous ECG variables. Cohort stringency is assured by elimination of outliers using a quantile regression model and clinical assessment with clearly abnormal values as outlined above. In order to develop predictive models, all ECG variables are analyzed in correlation to weight, height and BSA (calculated using the Dubois formula). In every age group, BSA shows consistent and significant correlation with selected ECG variables, therefore Z-score values are developed using BSA measurements. Prediction model comparison of fit statistics using Akaike information criterion is performed for linear, logarithmic, exponential, power and square-root models, and demonstrates that the power model is the most reliable. Accordingly, the power model is used to generate the distribution diagrams and tables of normative ECG standards. The data from the entire database is then transformed with a power regression for BSA to generate the new indexed normative standards. Z-scores are created from these novel predictive models, and critical cut-off values are calculated for each variable corresponding to Z-scores −2.5, −2, −1, 0, 1, 2, and 2.5. These cut-off values comprise the basis of normal ECG variables of healthy individuals (See, FIGS. 4A-4F, for example).

Figure 4A:
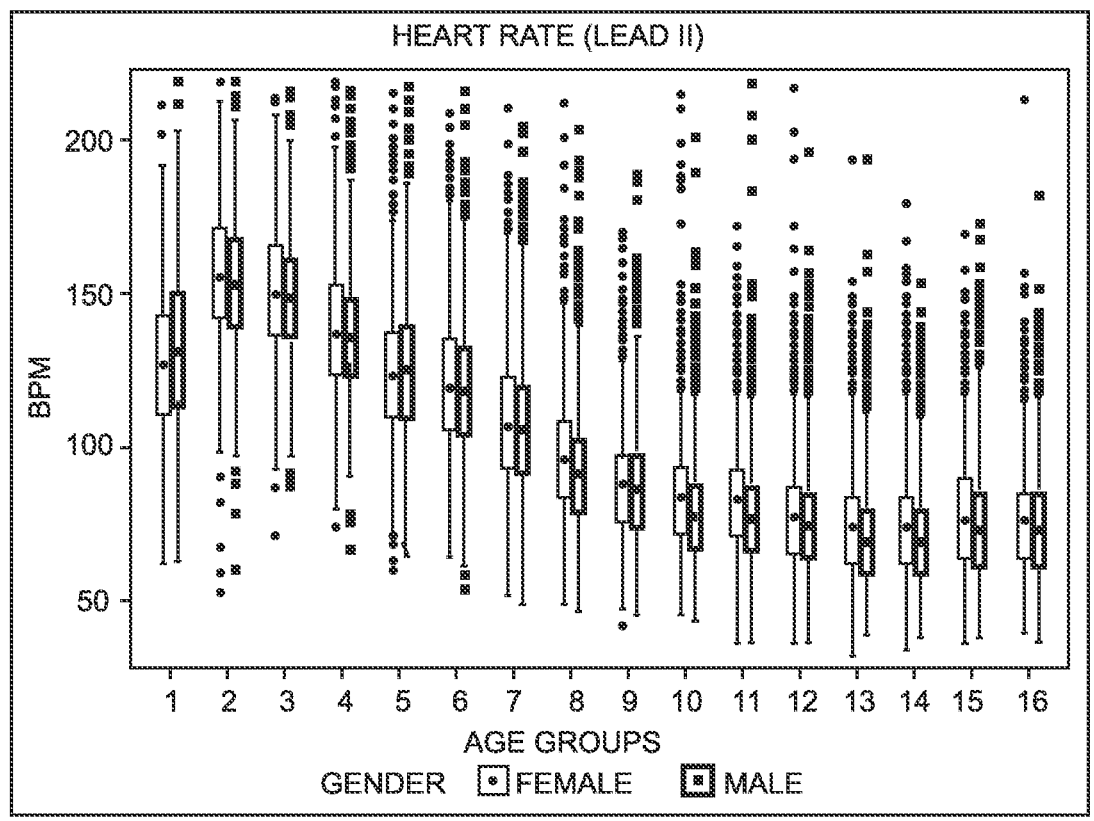
FIGS. 4A-4F are graphical representations of exemplary distributions of selected ECG variables over an age range of 0-39 years, according to aspects of the invention.
Figure 4B:
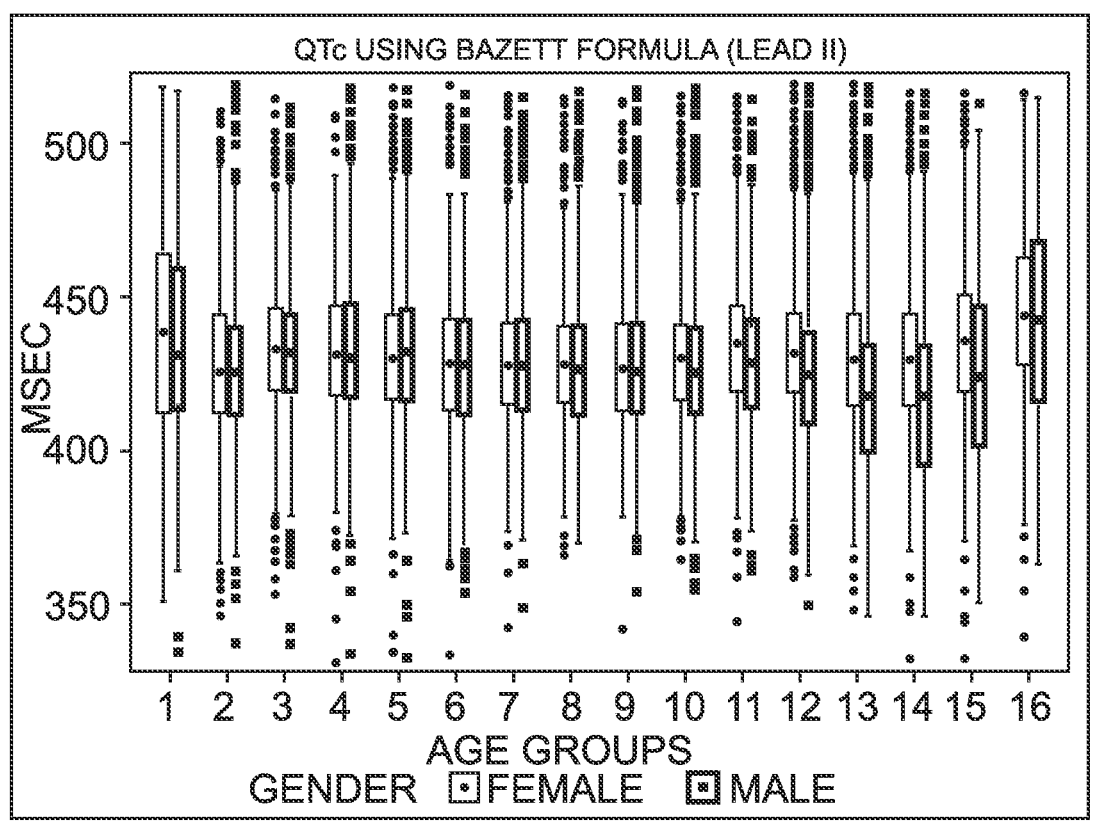
Figure 4C:
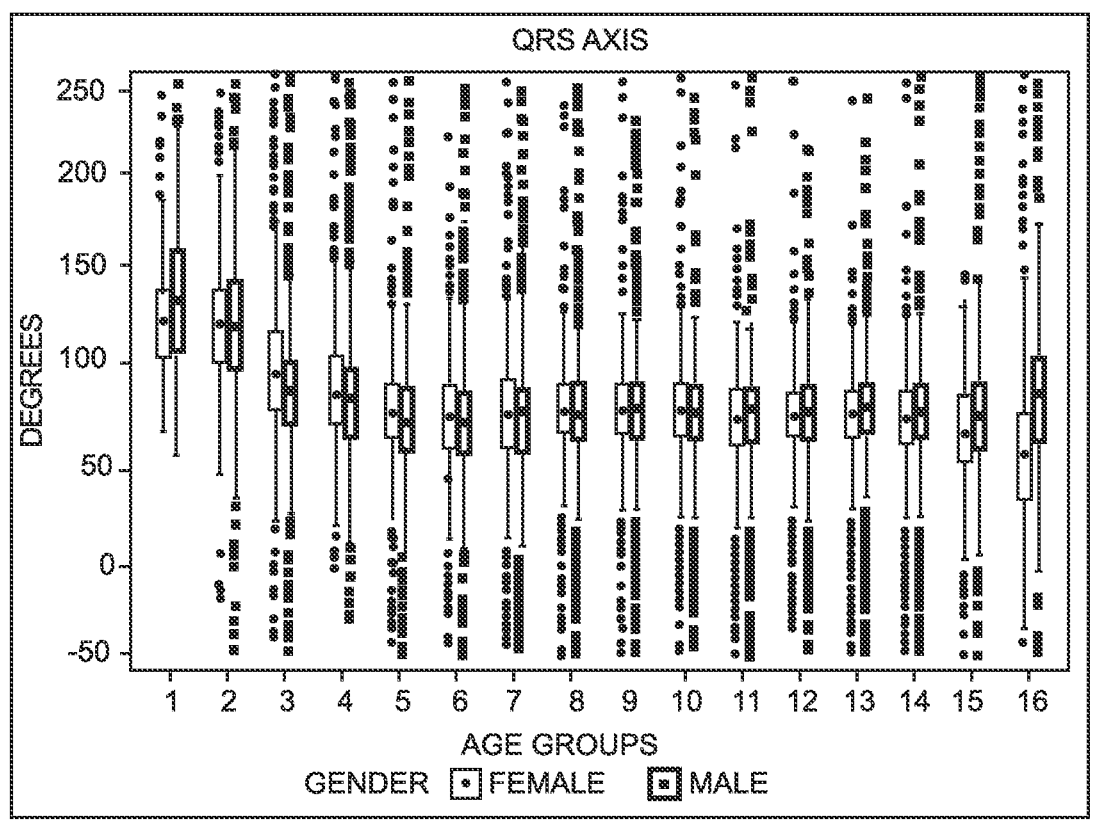
Figure 4D:
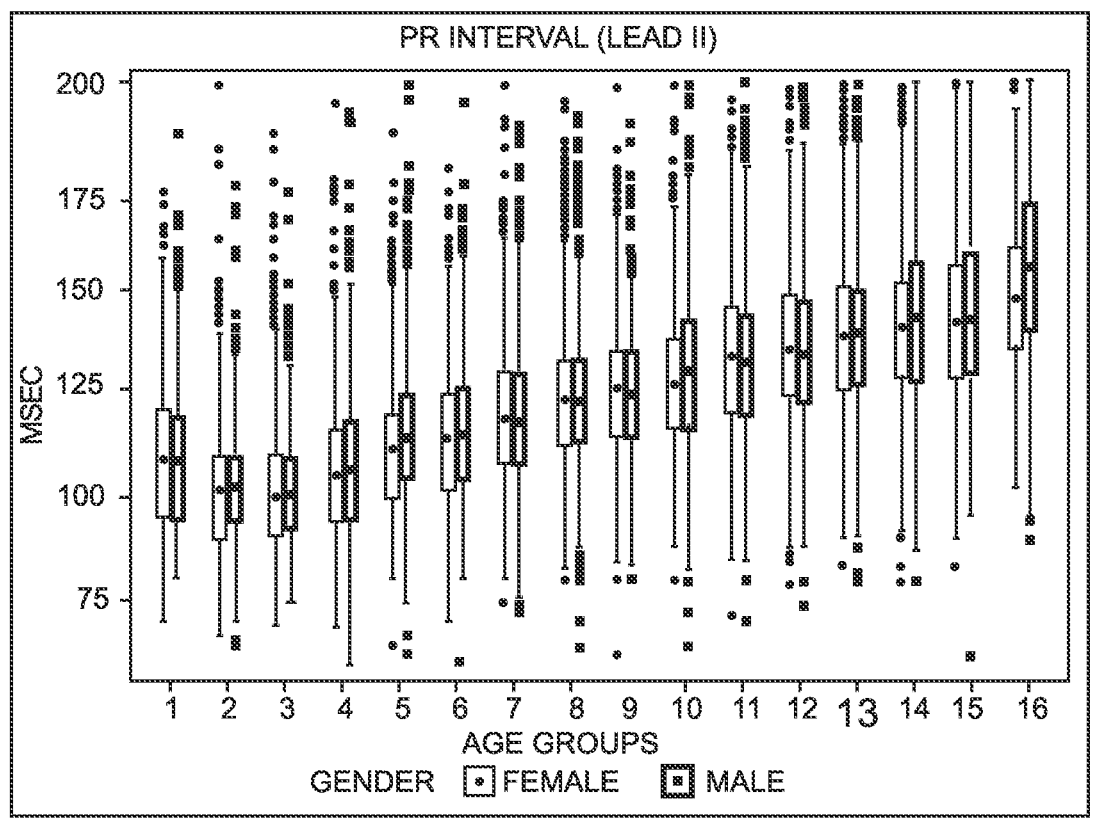
Figure 4E:
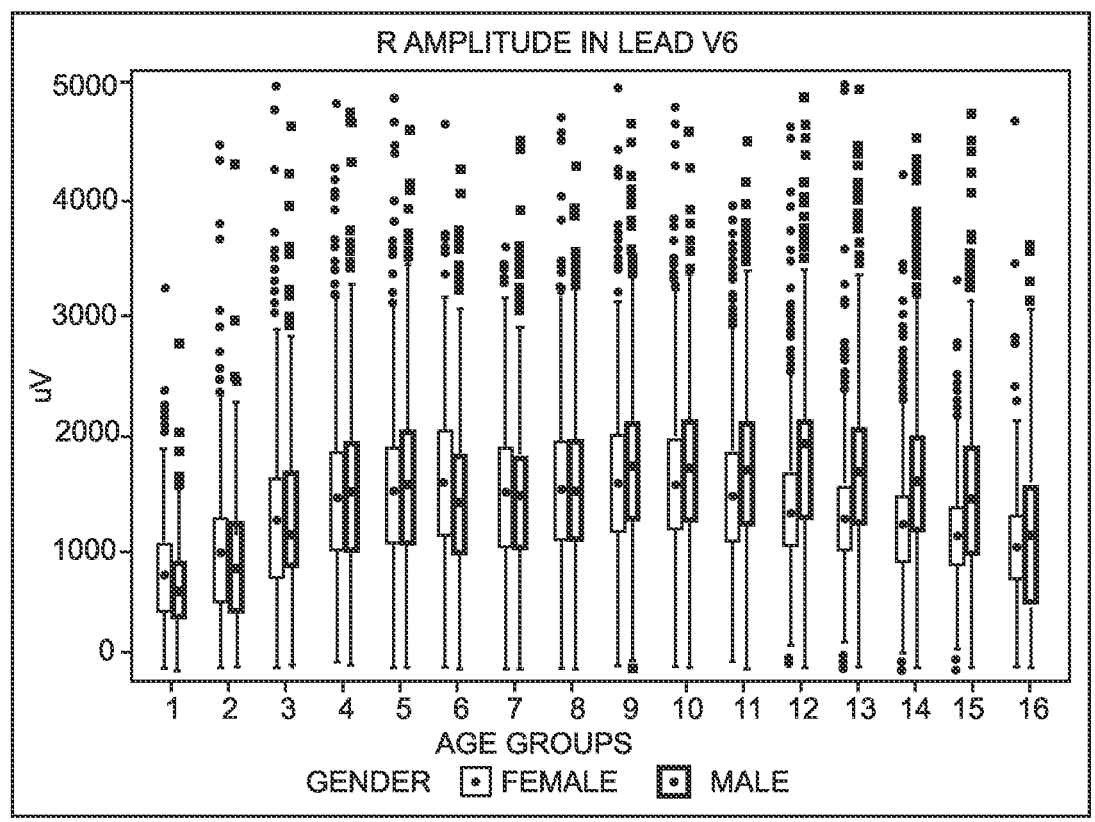
Figure 4F:
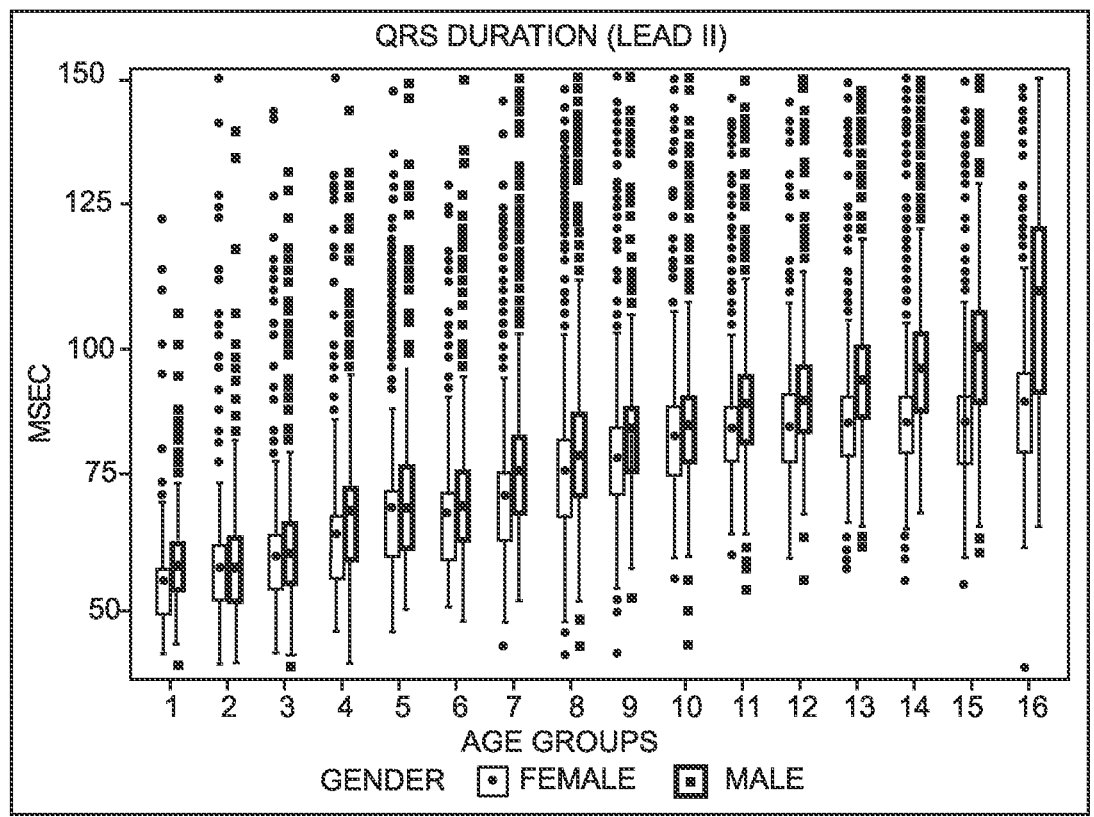

FIGS. 4A-4F are graphical representations of distributions of selected ECG variables over an age range of 0-39 years. Six ECG variables (heart rate, QTc Bazett, QRS axis, PR interval, R wave amplitude in V6, and QRS duration) are demonstrated using mean, median, interquartile range, and range, separated by 16 age groups and genders. Specifically, FIG. 4A depicts a distribution of heart rates over an age range of 0-39 years; FIG. 4B depicts a distribution of QTc using the Bazett formula over an age range of 0-39 years; FIG. 4C depicts a distribution of QRS axis over an age range of 0-39 years; FIG. 4D depicts a distribution of PR interval over an age range of 0-39 years; FIG. 4E depicts a distribution of R amplitude in lead V6 over an age range of 0-39 years; and FIG. 4F depicts a distribution of QRS duration over an age range of 0-39 years. In FIGS. 4A-4F, solid circles or squares correspond to mean, horizontal lines correspond to median, colored rectangular columns correspond to interquartile range, vertical lines with whiskers correspond with a range, and dots correspond with outliers.

Referencing FIGS. 4A, 4D and 4F, heart rate showed a constant decrease along childhood and young adulthood, while PR and QRS intervals showed a constant increase. Referencing FIG. 4B, during the first week of life lower heart rate and longer QTc values were observed compared to the following week. Females had slightly longer QTc than males starting from teenage years. Interestingly, the QRS duration was significantly shorter in females along all ages. See FIG. 4F. The QRS axis decreased after the first month of life as right ventricular electrical forces decrease, while the R wave amplitude in V6 showed a gradual increase until teenage years. See FIGS. 4C and 4E. Males had larger R wave voltages in V6 and more rightward QRS axis from teenage years. See FIGS. 4E and 4C.

The analysis of commonly used ECG variables is described here.

Heart rate: Almost all ECG variables show age-dependent differences. As expected, the average heart rate shows a gradual decrease from infancy to adulthood, starting at around 150 bpm (beats per minute), decreasing to around 75 bpm. During the first week of life, the average heart rate is about 25 bpm lower compared the second week of life. Females show slightly higher heart rate along almost all ages, for example, a heart rate of 76 bpm corresponds to a Z-score of −2 for newborn females, serving as a standard for bradycardia in this age group.

PR Interval: The PR interval gradually increases from infancy to adulthood. There are no significant differences by gender. In newborn females for example, a PR interval of 67 milliseconds (msec) yields a Z-score of −2, and 144 msec yields a Z-score of +2, providing the basis of determination for interpretations of "short PR" and first degree atrioventricular block, respectively, for this age group. By early teenage years (12-13 years), "short PR" and first degree atrioventricular block would correlate to 100 msec and 172 msec, respectively.

QRS duration: The QRS duration shows a continuous increase from infancy to adulthood. Male subjects have a slightly longer QRS duration along all ages, which difference becomes more pronounced after 10 years of age, and continues to young adulthood. Therefore, the upper limits of normal for females and males in the 18-21 years age bracket are different, 106 msec for females, and 126 msec for males.

QT assessment: The QT and QTc values are longer in the 1-6 day group (Z-score 2 correlated to QTc 508-511 msec) then the following age groups (Z-score 2 QTc 480-484 msec), remain similar during childhood until early teenage years, where the values again show statistically significant increase in every age group, and a gender-dependent separation is observed. Female subjects show a slight increase in QTc values beginning at 8 years of age (significant difference between males and females in age groups 10-16, ages 8-39 years, e.g.: Z-score 2 in the 16-17 years age group correlated to QTc 476 msec in females and 464 msec in males). In the oldest age group, 21-39 years, the female-male difference is less pronounced, but still significant.

QRS axis and T wave axis: The average R wave axis decreases during the first 6 months of life from 120-130 degrees at birth to 70-80 degrees, then remains unchanged until young adulthood. In the older age groups, the R axis continues to decrease in females, and remains unchanged in males. Left axis deviation on ECG, for example in a teenage 14 year-old female, would then be a value under 29 degrees. The T wave axis remains similar along all age groups, with a minimal decline in males in adulthood. As a result of the temporal changes of the R and T wave axes, the values for a normal R-T axis deviation demonstrates a larger difference in early infancy, remaining unchanged through the rest of childhood, and further decreases in adult males.

R wave and S wave amplitudes: The precordial R and S wave amplitudes demonstrate age-dependent changes consistent with known structural changes observed in the right and left ventricle, especially during the first year of life. R wave amplitudes increase in V6 by 6 months of age, remain unchanged for the rest of childhood including adolescence, and decrease by adulthood. The average R wave value in V1 continues to decrease along childhood and adolescence in both genders. A maximum R in V6 for example, in a 16 year-old female and male, would be 2.12 mV and 3.09 mV, respectively, to assist in an ECG diagnosis of implied left ventricular hypertrophy.

Novel ECG Machine

Figure 5:
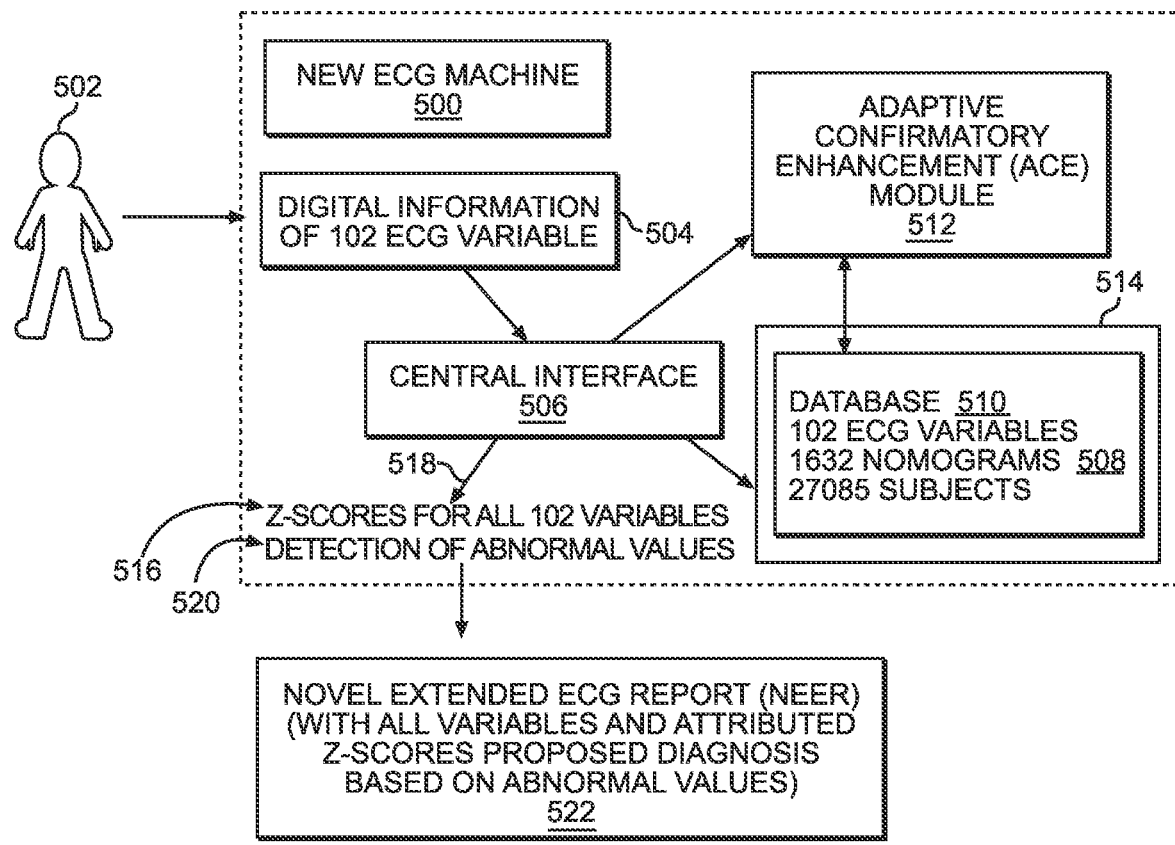
FIG. 5 is a diagram illustrating a system including a computer interface connected to a database and nomograms in accordance with aspects of the invention.

A novel ECG machine is created to perform the analysis of ECGs based on the novel Z-scores and predictive values (See, FIG. 5, for example).

FIG. 5 is a diagram illustrating a system including a computer interface connected to a database and nomograms. An actual patient connected to a 12-lead ECG machine 500 is represented at 502. Digital information of 102 ECG variables represented at 504 is obtained from the patient 502 and provided to a central interface indicated at 506. The graphical display of the computer interface in FIG. 5 shows how the patient's ECG data 504 are referenced against nomograms 508 of the database 510. In addition, the computer system of ECG machine 500 is equipped with an adaptive confirmatory enhancement (ACE) module 512 that can integrate further normative as well as abnormal data to improve the accuracy of ECG evaluation.

In implementations, a memory 514 of the ECG machine 500 stores the digital database 510 for the 102 ECG variables from 27085 subjects with 2,762,670 digital data points and 3264 Z-score-based nomograms.

This ECG machine 500 is connected to the standard 12 electrodes (not shown) to detect the electricity generated by the heart of an examined subject (new patient). The 12 leads are positioned on the patient 502 based on established standards. The electricity detected by the electrodes is transformed to digital values of the 102 ECG variables in the ECG machine. The values of each ECG variable are then weighed against the 102 Z-score-based nomograms in the appropriate gender and age group. A computer-based algorithm analyzes the values of the examined subject 502 and calculates the predicted Z-scores 516 for every ECG variable, as represented at 518. Following the determination of Z-scores, the computer interface 506 with the evaluation algorithm identifies all the values beyond normal limits 520 and links the appropriate suggested diagnosis correlating to the abnormal value 520 of the ECG variable. The standard 12-lead ECG with the waveforms, the absolute value of the 102 ECG variable, the predicted Z-scores 516 attributed to every ECG variable, and the evaluation of the abnormal ECG variables 520 with suggested diagnoses are generated (e.g., by a report generator unit not separately shown) for a NEER 522. See, for example, the NEER 522 of FIG. 5, including all variables and attributed Z-scores and proposed diagnosis based on abnormal values.

Computer Interface with Adaptive Confirmatory Enhancement (ACE) Module for ECG Analysis With reference to FIG. 5, the computer interface or central interface 506 is the central computational unit of the ECG machine 500 connecting the obtained data from the examined subject 502, the memory 514 with the database 510, the ACE module 512 and the report generator unit (not separately shown).

The electrical data from an examined subject (new patient) is converted to digital data. The digital data is then recorded for all 102 ECG variables and passes through the computer interface 506. The computer interface 506 compares the digital data in each of the 102 ECG variables to the normative standards from the database 510. The database 510 with the normal values and nomograms for 102 ECG variables serves as a reference value for ECG interpretation. A computer-based algorithm compares the new patient data to the nomograms 508 and calculates the predicted Z-score 516. Once the calculated Z-scores 516 are determined for each of the 102 ECG variables for the examined subjects, the ECG variables with abnormal values (i.e. Z-scores below −2 or above 2) are separated for the report (NEER 522). See, for example, the detection of abnormal values 520 in FIG. 5. Based on the list of ECG values that are abnormal, the (ACE) module 512 selects the appropriate list of ECG diagnoses. The information is than passed into the report generator unit (not separately shown), which creates a NEER 522 as described below.

The computer-based algorithm uses the ACE module 512 that is able to assess each ECG variable and determine normal and abnormal values and develop suggested diagnoses. In addition, this model is periodically curated by incorporating readings of prescreened normal and abnormal ECG values, verified by medical professionals, to further enhance the power of the database 510 and thus continuously improves the accuracy of the interpretation of ECGs with Z-scores (e.g., 516). The database 510 and the program is unique in the sense that it adapts based on the increasing number of normal data incorporated in the system, and therefore increases its accuracy in calculating Z-scores 516 and predicting cut-off values to differentiate normal from abnormal. The ACE module 512 incorporates machine learning of patterns that are not yet discovered, but could be used as specific markers to discern normal and abnormal ECG values of certain ECG variables.

Novel Extended ECG Reporting (NEER)

Figure 6A:
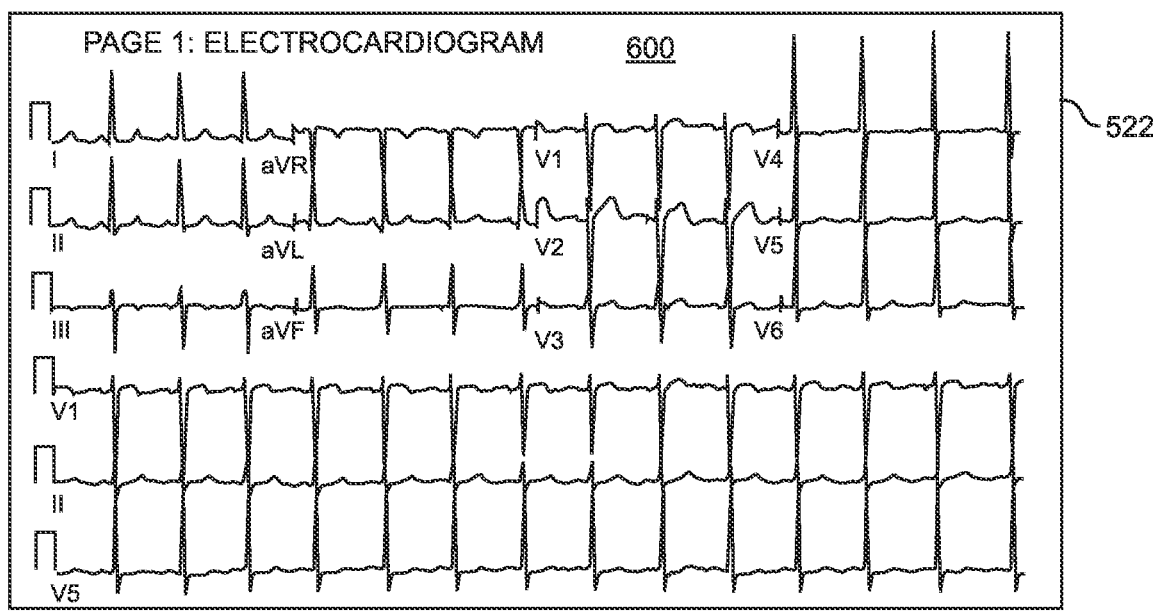

FIGS. 6A and 6B illustrate exemplary content of pages of a Novel Extended ECG Report (NEER) 522. A NEER 522 of an ECG will contain additional page(s) besides the standard 12-lead recording 600 depicted in page 1 of the NEER 522 in FIG. 6A. Further page(s) (e.g., page 2 of NEER 522 depicted in FIG. 6B) will indicate values of ECG variables with corresponding Z-scores 516 and abnormal variables 602 highlighted up front. The extended report 522 will correlate highlighted abnormal ECG variables 602 to a potential diagnoses (e.g., 604 of FIG. 6B), and may contain further information with predictive scores for specificity and sensitivity based on existing and future studies correlating ECG variables to cardiac disorders. See, for example, the information 606 in FIG. 6B showing a SV1 Z-score above 3 for LVH has a 70% specificity and 65% sensitivity.

With the improved power to examine quantitative variations in ECG measurements, we designed an extended ECG evaluation protocol: following the standard 12-lead ECG waveforms on the first page of the NEER 522, the proposed NEER 522 provides the practitioner with additional data for interpretation.

The second page of the NEER 522 depicted in FIG. 6B contains exact values and associated Z-scores of all 102 ECG variables. The values and Z-scores outside the range of norm (2 standard deviation below or above the norm, corresponding to a Z-score of less than −2 or more than 2) are outlined with bold letters as indicated at 602 in FIG. 6B. In addition, the NEER 522 contains suggested disease associations, based on quantitative ECG variable values outside the norm. See, for example, the diagnoses suggested at 604 in FIG. 6B. The NEER 522 will also include a predictive score 606 for the sensitivity and specificity of the variable cut-off values to certain diagnoses.

The calculation of the Z-scores and the predictive assessment on the second page of the ECG printout document (NEER) is generated by our computer-based evaluation program with the ACE module, which provides a continuously updatable and adaptable platform containing the normative data developed by an ever-expanding number of patients that the system interprets and incorporates into the existing database. The algorithm in the ACE module creates the ECG-disease associations based on a continuous machine learning to confirm and enhance the accuracy of suggested diagnoses.

Utilization of the Novel ECG System for Diagnosis and Screening

The ECG is used to detect cardiac problems in patients. Our novel ECG reporting revolutionizes the detection of cardiac conditions by clearly delineating normal and abnormal ECG values based on the largest historical cohort. Medical professionals assessing ECGs can rely on such enhanced reporting and therefore significantly improve the accuracy of their ECG interpretation.

Historically, medical professionals were required to determine normal and abnormal values based on their knowledge of cut-off values of ECG variables created by a small number of patients. Our more than 10-fold larger database and the automated detection of normalcy by predicted Z-scores provide the professionals a clear evaluation of 102 ECG variables. This automated detection can be used in large scale screening efforts aiming to evaluate thousands of ECGs without the necessary over-read of a medical professional. The enhanced power provided by the large database and Z-scores improve ECG reading accuracy and allow the development of organized screening programs relying on automated ECG reading.

The development of large scale automated ECG screening will have a marked influence on ECG screening programs for all individuals, athlete and non-athlete, in attempts to identify young people at risk of life-threatening events. The use of Z-scores should also help define more accurate cut-off values for improved specificity and sensitivity in all age groups.

The identification of abnormal S and R wave amplitudes with Z-scores exceeding 2 may yield a better delineation of normal and abnormal values and reflect the presence or absence of left ventricular hypertrophy. Hypertrophic cardiomyopathy (HCM), being the most commonly diagnosed cause of sudden cardiac death in youth, is suspected by abnormal R wave voltages in left lateral leads or abnormal S wave voltages in right precordial leads. Early work shows an extremely poor sensitivity, specificity, positive and negative predictive value of standard use ECG measurements in the identification of individuals with left ventricular hypertrophy found by echocardiography. Using "cut-off" values suggested by predicted Z-scores for specific age groups from our current evaluation process will enhance the rate of detection of HCM, and will improve the specificity and sensitivity of screening efforts for this particular diagnosis.

In addition, the current dataset provides standards for ECG variables never assessed before, such as the R-T axis deviation, the QRS integral, and T wave integral. The R-T axis difference, or T wave axis deviation, could be used to identify ventricular strain that may be present in patients with cardiomyopathy or hypertension, and therefore could also be useful in ECG screening. The summated integral of the QRS complex is a known indicator of mechanical interventricular asynchrony, and could be used to target resynchronization therapy. The establishment of normal T wave integral values could be useful for conditions affecting the myocardial repolarization, and its value could be used in discriminating patients with various forms of cardiomyopathy, and channelopathies like long QT syndrome.

Innovation of the Invention

The new normative ECG standards are based on the largest cohort ever compiled. The granular dataset of normal individuals separated by gender, into 16 discrete age groups, using electronic data acquisition and transformation provide the first detailed, truly quantitative assessment of ECG values in children and young adults. Z-scores are used for the first time in the evaluation of the standard 12-lead resting ECG. The calculated cut-off values expressed as Z-scores now lend an objective and reproducible evaluation of the ECG regardless of age and gender, and provide a simplified and reproducible determination of normalcy and abnormality. The database containing the normal values of more than 27,085 subjects created 3264 nomograms never available before. This database and the computer interface for the assessment of ECG values provide a breakthrough in the method of ECG evaluation. The entire enterprise is housed in the new ECG machine, which creates the novel extended ECG report allowing a new way of automated assessment of ECGs.

Significance of the Invention

Novel normative pediatric and young adult ECG standards with corresponding Z-scores, obtained from the largest historical cohort, create a reliable and reproducible evaluation of a wide range of ECG variables. Z-scores provide a consistent and easily recognizable limit that can be used for the overall assessment of the ECG with improved intrapersonal reproducibility and interpersonal consistency. Automated ECG reading results in a vastly improved ability to detect true variants from the normal range, understand differences by age, gender and body habitus and lay out the foundation for studies of ECG-disease correlations. ECGs that are read automatically with consistent accuracy provide the basis of high volume ECG screening for children and young adults. The development of a novel analysis and ECG report containing additional quantitative data generate invaluable additional information to health care providers for successful and consistent evaluation of the standard electrocardiogram and the prevention of sudden cardiac arrest or sudden cardiac death due to undetected heart conditions.

Potential Industrial Application and Change in Practice

The ECG is an inexpensive tool often used in widespread screening programs to detect electrical or structural heart defects in children and young adults. However the lack of specificity of prior used parameters, too few appropriately trained physicians to interpret results (pediatric electrophysiologists), the lack of interpersonal consensus and the lack of intrapersonal reproducibility undermine large scale screening efforts.

The current invention with normative data and reference Z-scores from the largest cohort and a novel concept of utilizing predicted Z-scores to support a breakthrough in the evaluation of ECGs. The automated computer assessment allows a high-throughput ECG screening separating the clearly abnormal measurements (with Z-scores below −2 and above 2) for further assessment by specialized clinicians. Such an ECG machine can be widely used by hospitals, clinics, independent providers, urgent care centers, as well as schools and sport authorities aiming to evaluate or screen healthy individuals or patients with cardiac problems.

The current invention can change medical practice pattern in two ways: (1) the accurate computer-based assessment can immediately determine abnormal values if they are outside of Z-scores −2 and 2, and help the practitioner discover ECG abnormalities to develop an accurate diagnosis; (2) the accurate and reproducible automated evaluation can be used for large scale screening efforts replacing the very few qualified individuals to provide certified ECG readings.

The innovative ECG machine will help in developing accurate diagnosis and help reveal previously undetected heart conditions. With the appropriate steps in implementing exercise allowance and medication guidelines in newly diagnosed individuals, sudden cardiac arrest or death can be prevented due to potential heart rhythm problems. These innovative technologies may save a large amount of time for practitioners in the systematic evaluation of ECGs and provide the basis for significant cost-reduction in the overall medical care.

In implementations, an automated non-invasive method of assessment of cardiac status of an examined subject and determination of normalcy and abnormality of the cardiac status based on an electrocardiogram (ECG) utilizing a novel Z-score-based nomogram for 102 ECG variables is provided, wherein the method includes: a) a recording of a 12-lead standard ECG from the examined subject containing the 102 ECG variables; b) a digital transformation of electrical ECG values of the 102 ECG variables; c) a comparison of the 102 ECG variables from the examined subject with data stored in a database based on 27085 healthy individuals; d) a development and an assignment of novel Z-scores to the 102 ECG variables determined by the novel Z-scorebased nomograms; e) an establishment of a diagnosis of a possible cardiac condition of the examined subject based on a determination of the novel Z-scores being within normal limits or outside normal limits of the Z-score-based nomograms; and f) a utilization of the diagnosis in health care settings, hospitals, outpatient clinics and screening programs of sick or healthy subjects for a determination of health and disease depending on the established diagnosis.

In embodiments, the automated non-invasive method described above is based on the comparison of the ECG values from the ECG of the examined subject to a novel database, the database includes: a) a compilation of normative data from the 27085 healthy individuals with no known heart defect, aged 0 days to 39 years, 23064 children and 4021 adults, 49% female and 51% male, from a wide range of ethnicity; b) a stratification of the database of the 27085 individuals into 16 age groups (0-7 days, 1-4 weeks, 5-12 weeks, 3-5 months, 6-11 months, 12-23 months, 2-3 years, 4-5 years, 6-7 years, 8-9 years, 10-11 years, 12-13 years, 14-15 years, 16-18 years, 18-21 years, adults above 22 years) and 2 genders (male and female); c) a collection of the digitalized values of the 102 ECG variables from the individuals, including but not limited to the ECG variables of heart rate, P wave axis, R wave axis, T wave axis, R-T wave axis deviation, PR interval, QRS interval, QT interval, QTc interval calculated using the Bazett formula, P, Q, R, S and T wave amplitudes, QRS integral and T wave integral in all ECG leads (I, II, III, aVR, aVL, aVF, V1, V2, V3, V4, V5, V6); and d) a creation of 3264 of the novel Z-score-based nomograms from the 102 ECG variables from the 27085 individuals, one said nomogram for every of one of the 102 ECG variables in every one of the 16 age groups with every one of the 2 genders (102×16×2=3264).

In implementations, the automated non-invasive method described above utilizes attribution of novel predicted Z-scores to the values of the 102 ECG variables of the examined subject derived from the novel Z-score-based nomograms, including: a) a calculation of mean and standard deviations from the mean for the values of the 102 ECG variables; b) a transformation of each of the 102 ECG variables into a graphical display with percentile data weighed by BSA; c) an assignment of the novel predicted Z-scores of −2.5, −2, −1, 0, 1, 2 and 2.5, corresponding to $0.6^{th}$, $2.3^{rd}$, $15.9^{th}$, $50^{th}$, $84.1^{th}$, $97.7^{th}$ and $99.4^{th}$ percentiles of the detected ECG values from the subject to serve as cut-off values of normalcy and abnormality for the 102 ECG variables; and d) a determination of the normalcy or abnormality for every one of the 102 ECG variables based on the value of the Z-scores below the lower or above the upper limit of normal, determined by being below Z-score −2 or above Z-score 2.

In aspects of the invention, the automated non-invasive method described above enables the diagnosis of certain cardiac pathology based on the determination of normal and abnormal the Z-scores of the 102 ECG variables, including: a) an evaluation of the ECG variables with the Z-scores outside of normalcy; b) an assessment of existing literature suggesting the cardiac pathology based on the abnormality of the ECG variable detected in the examined subject; c) an attribution of the suggested diagnosis to the examined subject; and d) a documentation and presentation of the suggested diagnosis to be used by a health care professional.

Embodiments of the invention provide an ECG machine capable of recording ECG data from an examined subject and creating a novel ECG report for a diagnosis of possible cardiac pathology utilizing novel Z-score-based nomograms. In implementations, the ECG machine includes: a) an electronic unit connecting the ECG machine to the examined subject; b) a specialized memory unit to contain the novel Z-score-based nomograms of 102 ECG variables from 27085 healthy individuals; c) a computer interface system that provides the digital transformation of electrical values obtained by the electronic unit from the examined subject, and executes the comparison of digitalized ECG values of the 102 ECG variables with a database in the memory unit; d) an adaptive confirmatory enhancement (ACE) module that periodically integrates new data to the database to enhance an accuracy of the diagnosis and update the novel Z-score-based nomograms; e) a novel extended ECG report (NEER) that contains a graphical display of a 12-lead standard ECG and a further page(s) containing Z-scores to every one of the 102 ECG variables, and containing the suggested diagnosis based on a comparison of the ECG values of the examined subject to the database; and f) a housing unit developed for the housing of the electronic unit, the specialized memory unit, the computer interface system, the ACE modules and the NEER generator.

In embodiments, the ECG machine described above contains the specialized memory unit, further including: a) a raw value of the 102 ECG variables from the 27085 healthy individuals; b) a total of 2,762,670 data points of 3264 novel Z-score-based nomograms developed for the 102 ECG variables from the 27085 healthy individuals; c) the attributed values to the Z-scores of every one of the 102 ECG variables in every one of the 16 age groups for both 2 genders; and d) a summary of publications aiding in the diagnosis of possible cardiac pathology.

In implementations, the ECG machine described above contains the computer interface system that enables the method of diagnosing cardiac pathology and the determination of normalcy and abnormality of the 102 ECG variables, and the method includes: a) the digital transformation of the electrical values obtained by the electronic unit from the examined subject; b) an assessment of the examined subject's ECG values for the comparison of the ECG values to the database; c) an execution of the comparison of the digitalized ECG values of the 102 ECG variables with the database in the memory unit to the actual values of the examined subject; d) an interaction with the ACE module for expansion and enhancement of the database; and e) the generation of the NEER as a print-out from the housing unit.

In embodiments, the ECG machine described above contains the adaptive confirmatory enhancement (ACE) module for the periodic expansion and enhancement of data in the database, and further includes: a) an addition of novel ECG data from new subjects to be incorporated into the existing novel Z-score-based nomograms of the database to adapt the database; b) a confirmation and improvement in the accuracy of the Z-score derived cut-off values based on the extended database and normative data; and c) an enhancement of the suggested diagnosis by a machine learning algorithm that incorporates the ECG values of new examined subjects to the expanded database and constantly improves the accuracy of the suggested diagnosis by discerning normal and abnormal ECGs in order to perfect the interpretation of ECGs with the Z-scores.

In aspects of the invention, the ECG machine described above contains the novel extended ECG report (NEER) to provide the 12-lead ECG print-out with additional information to aid the development of confirmed ECG diagnosis by health care professionals, wherein the NEER includes: a) the graphical display of the 12-lead standard ECG; b) the further page(s) containing all measured ECG values for all the 102 ECG variables with corresponding calculated Z-scores; and c) and the further page(s) containing the suggested diagnosis and interpretation of the identified abnormal Z-scores with a likelihood ratio of possible diagnoses of cardiac pathology to be considered by the evaluating health care professional.

In embodiments, a process of prevention of sudden cardiac arrest and death for the examined subjects enabled by a diagnosis of cardiac pathology is provided based on the automated non-invasive method of assessment of cardiac status of an examined subject and determination of normalcy and abnormality of the cardiac status based on an electrocardiogram (ECG) utilizing a novel Z-score-based nomogram for 102 ECG variables. The process of prevention includes: a) the determination of existing cardiac pathology based on the suggested diagnosis; b) an establishment of guidelines for exercise allowance related to the cardiac pathology; and c) a delineation of steps for the process of prevention of sudden cardiac arrest or death in the examined subjects.

In implementations, the process of prevention described above is utilized in screening of individuals for the purpose of the implementation of preventive measures, the process including: a) an employment of the automated non-invasive process with the ECG machine for a conduction of large-scale screening of healthy or sick individuals for an aim of detection of unknown heart conditions; b) a development of high throughput screening for children and adults including screening prior to participation in sport clubs, school-related activities, non-school related activities, or screening programs established by volunteer groups; and c) the determination of the suggested diagnosis of possible cardiac pathology based on the evaluation of ECGs on a large scale for the individuals screened.

In embodiments, the process of prevention described above is utilized for the prevention of sudden cardiac arrest or death of the examined subjects, wherein process of prevention includes: a) the establishment of diagnosis that can result in sudden cardiac death; b) an implementation of a detailed exercise allowance protocol for the prevention of exercise related cardiac arrhythmias; c) a suggestion of personalized medical management of the examined subjects using antiarrhythmic medications for the prevention of ventricular arrhythmia that may lead to sudden cardiac arrest; and d) a detailed suggestion of medications to be avoided by the examined subjects in order to prevent the development of possible ventricular arrhythmia that may lead to sudden cardiac arrest.

The invention claimed is:

1. An automated non-invasive method of assessment of cardiac status of an examined pediatric subject utilizing an electrocardiogram (ECG) system including: an electronic unit configured to connect to the examined pediatric subject, a memory unit configured to contain a database of Z-score-based nomograms of a first set of ECG variables from historic data of healthy individuals including pediatric individuals, a computer interface system, an adaptive confirmatory enhancement (ACE) module, and a report generator, the method comprising:

digitally transforming, by the computer interface system of the ECG system, electrical values obtained by the electronic unit from the examined pediatric subject to generate digital ECG values of a second set of ECG variables of the examined pediatric subject;

determining, by the computer interface system of the ECG system, that the digital ECG values of the second set of ECG variables of the examined pediatric subject comprises abnormal R wave voltages in left lateral leads of the examined pediatric subject of the ECG system, wherein the abnormal R wave voltages comprise Z-scores with two standard deviations above a mean Z-score of the first set of ECG variables from the historic data of healthy individuals including the pediatric individuals or Z-scores with two standard deviations below the mean Z-score of the first set of ECG variables from the historic data of healthy individuals including the pediatric individuals;

executing, by the computer interface system of the ECG system, a comparison of the digital ECG values of the second set of ECG variables of the examined pediatric subject with the pediatric individuals in the database in the memory unit;

determining, by the computer interface system of the ECG system, a diagnosis of hypertrophic cardiomyopathy (HCM) of the examined pediatric subject based on the comparison;

periodically integrating, by the ACE module of the ECG system, new ECG data into the database by performing continuous machine learning to create ECG-disease associations and confirm and enhance an accuracy of the diagnosis of HCM of the examined pediatric subject by calculating new Z-scores and new cut-off values to predict a first set of new normal and abnormal ECGs using the continuous machine learning and update the Z-score-based nomograms based on the new Z-scores, the new cut-off values, and the first set of new normal and abnormal ECGs;

generating, by the report generator of the ECG system, an extended ECG report containing: a predictive Z-score for each one of the second set of ECG variables of the examined pediatric subject; and the diagnosis of HCM of the examined pediatric subject based on the updated Z-score-based nomograms;

incorporating, by the ACE module of the ECG system, a second set of new normal and abnormal ECG values of the second set of ECG variables by incorporating the continuous machine learning of undiscovered patterns that are used to discern the second set of new normal and the abnormal ECG values of the second set of ECG variables to further create the ECG-disease associations and enhance the accuracy of the diagnosis of HCM of the examined pediatric subject and further update the Z-score-based nomograms based on the second set of new normal and abnormal ECG values; and determining, by the ACE module of the ECG system, whether the diagnosis of HCM of the examined pediatric subject is accurate based on the periodic integration of the new ECG data into the database by performing continuous machine learning to create the ECG-disease associations and the incorporation of the second set of new normal and abnormal ECG values of the second set of ECG variables by incorporating the continuous machine learning of the undiscovered patterns that are used to discern the second set of new normal and the abnormal ECG values of the second set of ECG variables to further create the ECG-disease associations, wherein the examined pediatric subject and the pediatric individuals in the database comprise individuals up to an age of eighteen, the digital ECG values of the second set of ECG variables comprise T wave axis, R-Taxis deviation, T wave voltage, QRS axis, QRS integral, and T wave integral which are used in determining the diagnosis of HCM of the examined pediatric subject, the electronic unit connects an ECG machine to the examined pediatric subject, the ECG machine comprises the memory unit, and the computer interface system comprises the ACE module, and the first set of ECG variables comprise up to 102 ECG variables and the pediatric individuals of the historic data comprise up to 27,085 pediatric individuals.

2. The method of claim 1, wherein:

the digital ECG values of the second set of ECG variables of the examined pediatric subject include R wave voltages in left lateral leads of the ECG system or S wave voltages in right precordial leads of the ECG system; and the ECG system establishes the diagnosis by associating the abnormal R wave voltages in the left lateral leads of the ECG system or abnormal S wave voltages in the right precordial leads of the ECG system with the diagnosis.

3. An electrocardiogram (ECG) system comprising:

an electronic unit configured to connect an ECG machine to an examined pediatric subject, the ECG machine comprises a memory unit, and a computer interface system comprises an adaptive confirmatory enhancement (ACE) module;

the memory unit configured to contain a database of Z-score-based nomograms of a first set of ECG variables from historic data of healthy individuals including pediatric individuals;

a computer interface system configured to:
digitally transform electrical values obtained by the electronic unit from the examined pediatric subject to generate digital ECG values of a second set of ECG variables of the examined pediatric subject;

determine that the digital ECG values of the second set of ECG variables of the examined pediatric subject comprises abnormal R wave voltages in left lateral leads of the examined pediatric subject of the ECG system, wherein the abnormal R wave voltages comprise Z-scores with two standard deviations above a mean Z-score of the first set of ECG variables from the historic data of healthy individuals including the pediatric individuals or Z-scores with two standard deviations below the mean Z-score of the first set of ECG variables from the historic data of healthy individuals including the pediatric individuals;

execute a comparison of the digital ECG values of the second set of ECG variables of the examined pediatric subject with the pediatric individuals in the database in the memory unit; and determine a diagnosis of hypertrophic cardiomyopathy (HCM) of the examined pediatric subject based on the comparison;

the adaptive confirmatory enhancement (ACE) module configured to periodically integrate new ECG data into the database by performing continuous machine learning to create ECG-disease associations and confirm and to enhance an accuracy of the diagnosis of HCM of the examined pediatric subject by calculating new Z-scores and new cut-off values to predict a first set of new normal and abnormal ECGs using the continuous machine learning and update the Z-score-based nomograms based on the new Z-scores, the new cut-off values, and the first set of new normal and abnormal ECGs;

a report generator configured to generate an extended ECG report containing: a predictive Z-score for each one of the second set of ECG variables of the examined pediatric subject; and the diagnosis of HCM of the examined pediatric subject based on the updated Z-score-based nomograms;

the ACE module is further configured to incorporate a second set of new normal and abnormal ECG values of the second set of ECG variables by incorporating the continuous machine learning of undiscovered patterns that are used to discern the second set of new normal and the abnormal ECG values of the second set of ECG variables to further create the ECG-disease associations and enhance the accuracy of the diagnosis of HCM of the examined pediatric subject and further update the Z-score-based nomograms based on the second set of new normal and abnormal ECG values; and the ACE module is further configured to determine whether the diagnosis of HCM of the examined pediatric subject is accurate based on the periodic integration of the new ECG data into the database by performing continuous machine learning to create the ECG-disease associations and the incorporation of the second set of new normal and abnormal ECG values of the second set of ECG variables by incorporating the continuous machine learning of the undiscovered patterns that are used to discern the second set of new normal and the abnormal ECG values of the second set of ECG variables to further create the ECG-disease associations, wherein the examined pediatric subject and the pediatric individuals in the database comprise individuals up to an age of eighteen, the digital ECG values of the second set of ECG variables comprise T wave axis, R-Taxis deviation, T wave voltage, QRS axis, QRS integral, and T wave integral which are used in determining the diagnosis of HCM of the examined pediatric subject, and the first set of ECG variables comprise up to 102 ECG variables and the pediatric individuals of the historic data comprise up to 27,085 pediatric individuals.

4. The ECG system of claim 3, further comprising: a housing unit is a housing of the electronic unit, the memory unit, the computer interface system, the ACE module and the report generator.

5. The ECG system of claim 3, wherein the memory unit further comprises:

raw values of the first set of ECG variables from healthy individuals including the pediatric individuals;

data points of the Z-score-based nomograms developed for the first set of ECG variables from the healthy individuals including the pediatric individuals;

attributed values to the Z-scores of every one of the first set of ECG variables in every group of a plurality of age groups for two genders; and a summary of publications aiding in the diagnosis of HCM.

6. The ECG system of claim 3, wherein:

the Z-score-based nomograms of the first set of ECG variables from the historic data of healthy individuals including the pediatric individuals are based on Z-scores of the ECG variables from the historic data;

the Z-scores of the ECG variables from the historic data serve as cut-off values of normalcy and abnormality for each of the ECG variables from the historic data; and the adaptive confirmatory enhancement (ACE) module is further configured to:

improve an accuracy of the Z-score derived cut-off values based on the periodically integrating new data into the database, wherein the enhancing an accuracy of the diagnosis of HCM is performed by a machine learning algorithm that incorporates ECG values of newly examined pediatric subjects to the database to improve the accuracy of the diagnosis of HCM by discerning normal and abnormal ECGs in order to perfect an interpretation of ECGs with the Z-scores of the ECG variables from the historic data.

7. The ECG system of claim 3, wherein:

the report comprises the digital ECG values of the second set of ECG variables of the examined pediatric subject for the 102 ECG variables;

the predictive Z-score for each one of the second set of ECG variables in the report comprises a predictive Z-score for each one of the 102 ECG variables; and the report further comprises a graphical display of an ECG waveform, and an interpretation of identified abnormal Z-scores of the examined pediatric subject with a likelihood ratio of the diagnosis of HCM.

8. The ECG system of claim 3, wherein:

the digital ECG values of the second set of ECG variables of the examined pediatric subject include S wave voltages in right precordial leads of the ECG system; and the ECG system establishes the diagnosis by associating the abnormal R wave voltages in the left lateral leads of the ECG system or abnormal S wave voltages in the right precordial leads of the ECG system with the diagnosis.

9. The ECG system of claim 3, wherein the Z-score-based nomograms are determined based on body surface area measurements.

10. The ECG system of claim 3, wherein the extended ECG report further contains 12-lead ECG waveforms, the digital ECG values of all the ECG variables of the first set of ECG variables and the second set of ECG variables, and specificity and sensitivity of at least one of the predictive Z-scores.

11. The ECG system of claim 3, wherein the Z-score-based nomograms comprise a graphical display of normal values.

12. The EGC system of claim 3, wherein the Z-score-based nomograms are generated by:

calculating a mean and standard deviations from a mean for digital values of normative ECG variables;

transforming the digital values of the normative ECG variables for each of the ECG variables into a normal distribution graph with percentile data weighed by body surface area;

assigning the Z-scores to percentiles of the normal distribution graph of each of the ECG variables; and creating a nomogram for each of the ECG variables in relation to the body surface area based on the assigned Z-scores, thereby generating the Z-score based nomograms.

13. The ECG system of claim 12, wherein the Z-scores serve as cut-off values of normalcy and abnormality for each of the normative ECG variables, and the computing interface is further configured to determine that the predictive Z-scores are within normal limits or are outside normal limits of the Z-score-based nomograms.

14. The ECG system of claim 12, wherein the healthy individuals comprise the pediatric individuals with no known heart defects and normative data of the Z-score-based nomograms is stratified into a plurality of age groups and by gender.

15. The ECG system of claim 3, wherein the predicted Z-scores are each selected from the group consisting of: −2.5, −2, −1, 0, 1, 2 and 2.5.

16. The ECG system of claim 3, wherein the extended ECG report further contains a graphical display of an ECG waveform, and an interpretation of identified abnormal Z-scores of the examined pediatric subject with a likelihood ratio of the diagnosis of HCM.

17. The ECG system of claim 3, wherein extended ECG report further comprises highlighted ECG variables and predictive Z-scores outside a range of norm.

18. The ECG system of claim 3, wherein the ECG variables of the first set of ECG variables and the second set of ECG variables comprise: heart rate; P wave axis; R wave axis; the T wave axis; the R-T wave axis deviation; PR interval; QRS interval; QT interval; QTc interval calculated using the Bazett formula; P, Q, R, S and T wave amplitudes; the QRS integral and the T wave integral in all ECG leads.

* * * * *